United States Patent
Runeman et al.

(10) Patent No.: US 6,187,990 B1
(45) Date of Patent: Feb. 13, 2001

(54) INHIBITING THE GROWTH OF BACTERIA IN ABSORBENT ARTICLES BY ADDING OTHER BACTERIA

(75) Inventors: Bo Runeman, Josered; Rolf Andersson; Ulla Forsgren-Brusk, both of Mölnlycke; Stig Holm; Eva Grahn Håkansson, both of Umeå, all of (SE)

(73) Assignee: SCA Molnlycke AB, Gothenburg (SE)

(*) Notice: Under 35 U.S.C. 154(b), the term of this patent shall be extended for 0 days.

(21) Appl. No.: 09/000,326

(22) PCT Filed: Jul. 2, 1996

(86) PCT No.: PCT/SE96/00891

§ 371 Date: Feb. 18, 1998

§ 102(e) Date: Feb. 18, 1998

(87) PCT Pub. No.: WO97/02846

PCT Pub. Date: Jan. 30, 1997

(30) Foreign Application Priority Data

Jul. 13, 1995 (SE) .................................................. 9502588

(51) Int. Cl.$^7$ ............................. A61F 13/15; A61F 13/20
(52) U.S. Cl. ..................... 604/360; 604/358; 604/367; 604/385.01
(58) Field of Search ............................... 604/385, 385.1, 604/385.2, 385.01, 358, 359, 360, 367

(56) References Cited

U.S. PATENT DOCUMENTS

| 3,794,034 | 2/1974 | Jones, Sr. . |
| 4,589,876 | * 5/1986 | Van Tilburg ......................... 604/385 |
| 4,983,163 | 1/1991 | Winans, Jr. et al. . |

FOREIGN PATENT DOCUMENTS

| 1298556 | 4/1992 | (CA) . |
| 2 309 575 | 9/1974 | (DE) . |
| 0 202 127 | 11/1986 | (EP) . |
| 0 311 344 | 4/1989 | (EP) . |
| 0 446 619 | 9/1991 | (EP) . |
| 2 143 738 | 2/1985 | (GB) . |
| 8 505 491 | 5/1987 | (SE) . |
| WO 91/12031 | 8/1991 | (WO) . |
| WO 92/13577 | 8/1992 | (WO) . |
| WO 93/09793 | 5/1993 | (WO) . |

OTHER PUBLICATIONS

By Gregor Reid, "Applications for bacterial adhesion and biofilm studies in relation to urogenital tissues and biomaterials: A review", *Journal of Industrial Microbiology*, vol. 13, 1994, pp. 90–96.

By Gregor Reid, "Adhesion of lactobacilli to urinary catheters and diapers: Effect of surface properties", *Journal of Biomedical Materials Research*, vol. 28, 1994, pp. 731–734.

(List continued on next page.)

*Primary Examiner*—John G. Weiss
*Assistant Examiner*—Miley Craig Peppers
(74) *Attorney, Agent, or Firm*—Young & Thompson

(57) ABSTRACT

The invention relates to absorbent articles, such as diapers and like articles and is concerned with methods for preventing undesirable odors and/or preventing the growth of undesirable microorganisms when the articles are in use, and also provides an absorbent article which can be worn for long periods of time without generating undesirable odors, incurring the risk of infection or having a negative effect on skin. Another object is to amplify the presence in the wearer's urogenital zone of microbiological flora that will assist in preventing the occurrence of urinal tract infections. These objects have been achieved by adding to the absorbent articles microorganisms which exhibit antagonistic properties against present undesirable strains of microorganisms, so as to restrain the growth of these or establishing of new undesirable species.

12 Claims, 1 Drawing Sheet

OTHER PUBLICATIONS

By Christine C. Sanders et al., "Toxic shock syndrome: An ecologic imbalance within the genital microflora of women", *American Journal of Obstetrics and Gynecology*, vol. 142, 1982, pp. 977–982.

By G. Reid et al., "Influence of lactobacilli on the adhesion of *Staphylococcus aureus* and *Candida albicans* to fibers and epithelial cells", *Journal of Industrial Microbiology*, vol. 15, 1995, pp. 248–253.

* cited by examiner

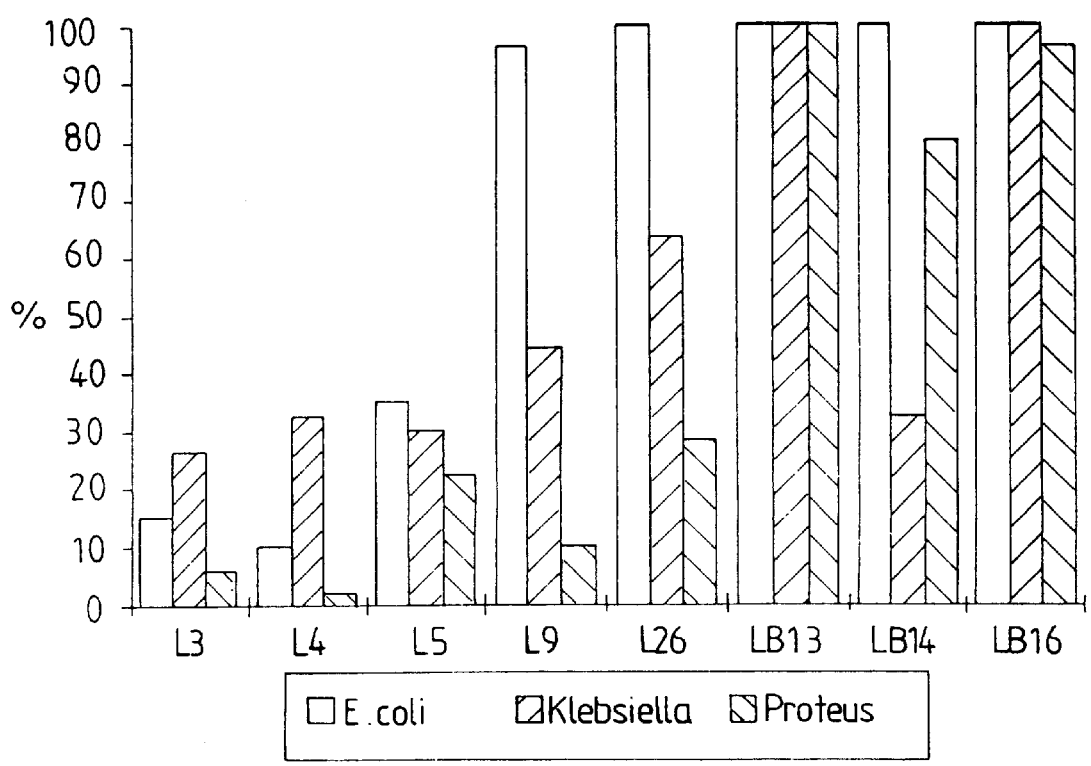

INHIBITING THE GROWTH OF BACTERIA IN ABSORBENT ARTICLES BY ADDING OTHER BACTERIA

TECHNICAL FIELD

The present invention relates to absorbent articles such as diapers, incontinence guards, sanitary napkins and like articles, and is concerned with methods of preventing the generation of undesirable odors and/or the growth of undesirable microorganisms as the article is worn.

PROBLEMS

Many designs of absorbent articles of this kind are known to the art. Conventionally, the absorbent body of such articles is produced by dry-defibering cellulose pulp contained for instance in rolls, bales or sheets, and transforming the fluffed pulp to a pulp mat, sometimes while admixing so-called superabsorbents, which may be polymers capable of absorbing several times their own weight in water or body fluid.

The absorbent body may also include other components, for instance components that will improve the ability of the absorbent body to take-up and disperse liquid, and that will increase its coherency and its ability to resist deformation in use.

Articles of this kind are liable to generate undesirable odors when in use, caused among other things by microbial metabolism, biological or chemical decomposition of components in body fluids, such as urine or menstruation fluid, for instance.

Another problematic area associated with the use of absorbent articles is the risk of infection caused by pathogenic microorganisms.

Another problem is found in the working environmental risks that can arise when handling soiled diapers that contain a large quantity of microorganisms. The growth of microorganisms that can take place in a soiled, used diaper during its storage after use can contribute to elevated odor problems and can also increase the risk of spreading undesirable microorganisms.

Another problem is the different forms of skin irritation and skin infections that can be caused directly or indirectly by microorganisms.

Microorganisms or their products that are known to contribute to the occurrence of undesirable odors, to cause infections in the urinal tract or to be associated with the occurrence of skin problems are, for instance such microorganisms as Proteus, Pseudomonas, Escherichia, Klebsiella, Enterococcus, Staphylococcus, Streptococcus and Candida.

DESCRIPTION OF THE KNOWN PRIOR ART

Different methods of alleviating the aforedescribed problems have been proposed. The International Patent Applications WO 91/11977 and WO 91/12031 describe methods of adsorbing undesirable odors in zeolite included in the absorbent article. U.S. Pat. No. 4,385,632 describes the addition of copper salt to a diaper with the intention of preventing the decomposition of urea to ammonia and therewith prevent the occurrence of unpleasant smells.

U.S. Pat. No. 3,794,034 describes the significance of pH in an absorbent article, and the significance of impregnating the article with a buffering substance by means of which the pH of the article can be maintained at between 3.5 and 6.0, which is advantageous from both the aspect of inhibiting the growth of undesirable bacteria, and therewith the generation of undesirable odors, and in avoiding a negative effect on the skin. European Patents EP 202127 and EP 311344 describe the adjustment of pH in absorbent articles that include superabsorbent material. Since buffering substances can have a negative effect on many superabsorbent materials, it is necessary to take separate measures to avoid undesirable effects. In the case of European Patent EP 202127, the superabsorbent material and buffering substances are placed in mutually separated zones in the absorbent article. In the case of European Patent EP 311344, the buffering and the superabsorbent properties have been combined in one and the same material, and a separate bacteria-inhibiting substance has also been added.

The drawback with these described methods is that when only an odor-absorbing agent is added, the bacteria are still able to grow, and the bacteria inhibiting agents, which are often selective, can create risks, for instance, in the form of allergenic properties or negative ecological consequences when handling waste. Furthermore, the use of this type of agent involves the risk that resistant strains will occur.

It is known within the medicine and foodstuff technologies to use bioconservation with the aid of bacterial antagonism as a conserving method, and to inoculate special bacteria strains to favourize bacteria populations that are beneficial to the stomach and intestines, for health-promoting purposes. Examples in this respect are conventional yoghurt and soured milk, and also novel bioactive foodstuffs. This methodology also includes the use of bacteria such as so-called probiotic bacteria as a substitute for antibiotic bacteria.

Canadian Patent CA 1,298,556 teaches the medical use of selected strains of lactobacteria, wherein, among other things, whole cells or cell fragments of Lactobacillus are used to treat or preclude the occurrence of urinal tract infections. International Patent Application WO 93/09793 describes the use of lactobacteria and skimmed milk preparations for precluding or preventing urogenital infections. International Patent Application WO 92/13577 describes a tampon or sanitary napkin that has been impregnated with a culture of lactic-acid producing bacteria, preferably of the genus Pediococcus, isolated from healthy individuals. The tampon or sanitary napkin is intended for the prophylactic treatment of urogenital infections.

SUMMARY OF THE INVENTION

The object of the present invention is to provide an absorbent article of the kind mentioned in the introduction which will allow the article to be worn, even for a long period, without permitting microorganisms to grow or to become active to an extent such as to promote undesirable odors, to incur the risk of infection or to have a negative effect on the skin. Another object of the invention is to enable antagonistic microorganisms to be transferred to the wearer so as to amplify in the wearer's urogenital zone the occurrence of such microbiological flora as those that will assist in preventing the occurrence of urinary tract infection. These objects have been achieved in accordance with the invention by adding to the absorbent article microorganisms which exhibit antagonistic properties against present undesirable strains or arising undesirable strains of microorganisms present in the absorbent article or in the urogenital zone of the wearer during regular use of the absorbent article, wherein said microorganisms are added in an amount and have an activity such as to restrain the growth of undesirable species or establishing of new undesirable species of microorganisms.

BRIEF DESCRIPTION OF THE DRAWING

FIG. 1 illustrates in terms of percentage the proportion of different bacteria strains that exhibit inhibited growth in the presence of antagonistic strains.

DETAILED DESCRIPTION OF THE INVENTION

The object of the present invention is to provide an absorbent article of the kind mentioned in the introduction which will enable the article to be worn for a relatively long period of time without microorganisms being allowed to grow to an extent in which undesirable odors are generated, in which the risk of infection is created, or to an extent which will have a negative effect on skin. A further object of the invention is to enable antagonistic microorganisms to be transferred to the wearer so as to amplify in the wearer's urogenital zone the presence of microbiological flora that will assist in preventing the occurrence of urinal tract infections.

Bacteria that cause unpleasant smells may belong to, for example, the family Enterobacteriaceae, e.g. *Proteus mirábilis, Proteus vulgaris, Escherichia coli* and Klebsiella.

Bacteria that cause urinal tract infections may belong to, for example, the families Enterobacteriaceae and Micrococcaceae or the genus Streptococcus. Examples of species and genera are *Escherichia coli, Proteus mirábilis,* Enterococcus, Klebsiella, Staphylococcus and Streptococcus.

Microorganisms associated with skin infections are Ascomycetes, Pseudomonadaceae and Micrococcaceae and the genus Streptococcus, e.g. *Candida albicans,* Pseudomonas, Staphylococcus and Streptococcus.

The invention is based on microbiological antagonism. This implies that one microorganism or combinations of microorganisms inhibits/inhibit other microorganisms by competing for substrate, changing pH, forming enzymes, toxins, carbon dioxide, peroxides or antibiotics, so-called bacteriocines.

Antagonistic microorganisms may be naturally occurring microorganisms which are non-toxic and do not have any negative biological effect on humans, in the form of infections or skin changes.

Antagonistic microorganisms may also be produced biotechnically.

The addition to an absorbent article of microorganisms which exhibit antagonistic properties against such undesirable strains of microorganisms that are present when the absorbent article is worn regularly, is able to restrain the growth of these undesirable strains of microorganisms or establishing of new undesirable strains. Even some killing of microorganisms of undesirable species may occur. It is necessary for the microorganisms to have an activity and to be added in amounts which will achieve the desired effect. Normally, this effect is achieved when the number of antagonistic microorganisms per absorbent article exceeds $10^6$ cfu, preferably $10^8$ cfu, more preferably $10^9$ cfu. By regular use is meant in this case daily use of an article with the article replaced several times during a calendar day, as is the case with products intended for use with children or incontinent adults. The term regular use may also include the use relevant to sanitary napkins or tampons during a menstruation period.

One advantage afforded by the use of antagonistic microorganisms is that there is avoided an undesired selection pressure on the micro environment, such as favouring potential disease-promoting microorganisms and therewith the risk of developing pathogenic strains that are resistant to antibiotics and chemopharmaceutical preparations. Since the antimicrobial system is based on a natural, biological process, there is less risk of environmental ecological and toxic disturbances.

An antagonistic strain shall exhibit a growth-inhibiting effect on several of the aforesaid undesired microorganisms, with conventional interference techniques.

A desired antagonistic microorganism shall also be capable of surviving in storage and to retain its growth ability or its ability to retain its activity in the absorbent article when worn.

The microorganisms that exhibit antagonistic properties may be bacteria or other microorganisms, for instance fungi. When the antagonistic microorganisms are bacteria, these bacteria are preferably selected from the family Lactobacillaceae and particularly from the genera Lactobacillus or Lactococcus and preferably from the species *Lactobacillus acidophilus, Lactobacillus curvatus, Lactobacillus plantarum* or *Lactococcus lactis.*

An absorbent article produced in accordance with the invention may include a permeable outer sheet which is intended to lie proximal to the wearer in use, a preferably liquid-impermeable backing sheet which is intended to lie distal from the wearer in use, and an absorbent structure placed between the outer sheet and the backing sheet. In some cases, an additional sheet in the form of, e.g., wadding or like material, may be placed between the outer sheet and the absorbent structure. The microorganisms exhibiting antagonistic properties may be placed in different parts of the absorbent article, for instance in the outer sheet, in the absorbent structure of the absorbent article, between two of the layers in the absorbent article, in a loose insert product in the absorbent article, or in some other way.

The following Examples illustrate the effect of antagonistic bacteria strains in more detail.

EXAMPLE 1

Synthetic urine to which a microorganism growth medium had been added was used as a test liquid. The synthetic urine contained monoions, divalent ions, cations and anions and urea and was prepared in accordance with information contained in Geigy, Scientific Tables, Vol. 1, 8th ed., 1981, p. 53. The microorganism growth medium was based on information concerning Hook and FSA media for enterobacteria.

EXAMPLE 2

Tests were carried out in accordance with the "agar overlay" method with the intention of studying bacterial antagonism. The method is based on the growth-inhibiting substance produced by the lactobacteria diffusing through an agar layer and inhibiting the growth of the test organisms.

Lactic acid bacteria, five strains of Lactobacillus and three strains of Lactococcus, were cultivated to an overnight culture in a suitable broth. Lactococcus were cultivated in M17 and Lactobacillus were cultivated in MRS. Agar (2%) of M17 and MRS (25 ml) respectively were mixed with 1.0 ml of respective bacteria and moulded in a petri dish. The Agar plates were incubated overnight at 37° C. The plates that contained MRS were incubated in a $CO_2$ atmosphere. Reference plates were prepared in a corresponding manner, but without lactic acid bacteria. A further layer containing 25 ml agar was moulded on top of the layer present in the petri dishes and allowed to solidify.

The test organisms, in the form of Gram-negative bacteria of respectively *Escherichia coli,* Klebsiella spp and Proteus spp, and 100, 91 and 50 strains respectively, were cultivated in a broth and a dilution corresponding to $10^7$ cfu/ml was prepared in a Bertani tray. The test bacteria were then stamped on the new agar layer with the aid of a so-called steers steel pin replicator. The plates were incubated at 37° C. for twenty-four hours. At the end of the incubation period, the plates were scanned and compared with the reference plates. "Growth", "inhibition" and "zero growth" were registered for respective test organisms when scanning the plates. All agar layers were measured with regard to pH, and plates having a pH beneath 5.0 were retested with pH-adjusted agar.

The results are listed in Tables 1–6 and shown in FIG. 1. The total number of test organisms that had been inhibited or given zero growth were calculated in percentage units. The results show that the growth of respective test organisms *Escherichia coli,* Klebsiella and Proteus was greatly inhibited by the presence of genera Lactobacillus while some inhibition was obtained in the presence of genera Lactobacillus.

TABLE 1

Test organism *Escherichia coli*

| Lactococcus No. | Growth number | Inhibition number | Zero growth number | Inhibition or zero growth |
|---|---|---|---|---|
| L 3 | 85 | 14 | 1 | 15 |
| L 4 | 91 | 9 | 1 | 10 |
| L 5 | 65 | 7 | 28 | 35 |
| L 9 | 4 | 0 | 96 | 96 |
| L 26 | 0 | 0 | 100 | 100 |

TABLE 2

Test organism *Escherichia coli*

| Lactobacillus No. | Growth number | Inhibition number | Zero growth number | Inhibition or zero growth |
|---|---|---|---|---|
| LB 13 | 0 | 0 | 100 | 100 |
| LB 14 | 0 | 2 | 98 | 100 |
| LB 16 | 0 | 2 | 98 | 100 |

TABLE 3

Test organism *Klebsiella spp*

| Lactococcus No. | Growth number | Inhibition number | Zero growth number | Inhibition or zero growth |
|---|---|---|---|---|
| L 3 | 68 | 16 | 7 | 25 |
| L 4 | 71 | 23 | 6 | 32 |
| L 5 | 64 | 10 | 17 | 29 |
| L 9 | 51 | 10 | 30 | 44 |
| L 26 | 34 | 36 | 21 | 63 |

TABLE 4

Test Organism *Klebsiella spp*

| Lactobacillus No. | Growth number | Inhibition number | Zero growth number | Inhibition or zero growth |
|---|---|---|---|---|
| LB 13 | 0 | 0 | 91 | 100 |
| LB 14 | 62 | 22 | 7 | 32 |
| LB 16 | 0 | 0 | 91 | 100 |

TABLE 5

Test organism *Proteus spp*

| Lactococcus No. | Growth number | Inhibition number | Zero growth number | Inhibition or zero growth |
|---|---|---|---|---|
| L 3 | 47 | 2 | 1 | 6 |
| L 4 | 49 | 1 | 0 | 2 |
| L 5 | 39 | 7 | 4 | 22 |
| L 9 | 45 | 4 | 1 | 10 |
| L 26 | 36 | 8 | 6 | 28 |

TABLE 6

Test organism *Proteus spp*

| Lactobacillus No. | Growth number | Inhibition number | Zero growth number | Inhibition or zero growth |
|---|---|---|---|---|
| LB 13 | 0 | 0 | 50 | 100 |
| LB 14 | 10 | 19 | 21 | 80 |
| LB 16 | 0 | 7 | 41 | 96 |

EXAMPLE 3

Five test products were produced, each consisting of a pulp body that comprised a fibre mixture of 50% chemithermomechanical cellulose pulp and 50% chemical cellulose pulp with an addition of about 5% superabsorbent material. The pulp body was sandwiched between a permeable nonwoven material having a surface weight of 23 g/m$^2$ and an impervious backing sheet comprised of 33 μm polyethylene film. A layer of polyester wadding having a surface weight of 65 g/m$^2$ was placed between the nonwoven sheet and the pulp body. A mixture of freeze-dried lactobacteria of genus Lactobacillus was placed between the wadding and the pulp body in an amount corresponding to $10^8$ bacteria per test product. 50 ml of synthetic urine according to Example 1 were then applied to the pulp body. The presence of lactobacteria in the groins and at the mouth of the urethra of five test subjects was measured, whereafter the subjects wore respective test products for two hours in the manner of a diaper or sanitary napkin. The presence of lactobacteria in the groins and at the mouth of the urethras of the test subjects was then again measured. The results are set forth in Table 7. It will be seen from the Table that the freeze-dried lactobacteria were activated when the test products were worn by the test subjects and that these lactobacteria were also transferred to the test subjects.

TABLE 7

| Test person | Start value urethra number lacto-bacteria | Start value groin number lacto-bacteria | After 2 hrs. urethra number lacto-bacteria | After 2 hrs. groin number lacto-bacteria |
|---|---|---|---|---|
| No. 1 | No growth | No growth | $3.6 \times 10^3$ | $1.5 \times 10^4$ |
| No. 2 | No growth | No growth | $2.8 \times 10^3$ | $2.7 \times 10^2$ |
| No. 3 | No growth | No growth | $1.4 \times 10^3$ | $8.4 \times 10^2$ |
| No. 4 | No growth | No growth | $3.8 \times 10^6$ | $4.0 \times 10^3$ |
| No. 5 | No growth | No growth | $4.5 \times 10^3$ | $8.6 \times 10^2$ |

It will be understood that the invention is not restricted to the illustrated and described exemplifying embodiment thereof and that other embodiments are conceivable within the scope of the following Claims.

What is claimed is:

1. In an absorbent diaper including added microorganisms, the improvement wherein the added microorganisms are selected from genera Lactobacillus or Lactococcus, and exhibit, when the absorbent diaper is worn regularly by a wearer for a short or longer period, antagonistic properties against undesirable strains of microorganisms from the families Enterobacteriaceae, Micrococcaseae, Psuedomonadaceae and Ascomycetes and the genus Streptococcus, and present or arising in the absorbent diaper or in the urogenital zone of the wearer of said absorbent diaper; and wherein the added microorganisms are added in such quantities and have such activity as to restrain the growth of undesirable species of microorganisms to such an extent as to prevent the generation of undesirable odors in the absorbent diaper.

2. The absorbent diaper according to claim 1, wherein the added microorganisms are antagonistic bacteria selected from species *Lactobacillus acidophilus, Lactobacillus curvatus, Lactobacillus plantarum* or *Lactococcus lactis.*

3. The absorbent diaper according to claim 1, wherein the number of added microorganisms per absorbent article exceeds $10^6$ cfu.

4. The absorbent diaper according to claim 3, wherein the number of added microorganisms per absorbent article exceeds $10^8$ cfu.

5. The absorbent diaper according to claim 4, wherein the number of added microorganisms per absorbent article exceeds $10^9$ cfu.

6. The absorbent diaper according to claim 1, wherein the added microorganisms are such that they exhibit antagonistic properties against one or several undesirable strains selected from species *Proteus mirabilis, Proteus vulgaris, Escherichia coli, Candida albicans* and the genera Klebsiella, Enterococcus, Staphylococcus, Streptococcus and Pseudomonas.

7. In an absorbent diaper comprising a permeable outer sheet which in use is intended to lie proximal to a wearer, a liquid-impermeable backing sheet which in use is intended to lie distal from the wearer, and an absorbent structure positioned between the outer sheet and the backing sheet, the absorbent diaper including added microorganisms, the improvement wherein the added microorganisms are selected from genera Lactobacillus or Lactococcus, and exhibit, when the absorbent diaper is worn regularly for a short or longer period, antagonistic properties against undesirable strains of microorganisms from the families Enterobacteriaceae, Micrococcaseae, Psuedomonadaceae and Ascomycetes and the genus Streptococcus, and present or arising in the absorbent diaper or in the urogenital zone of the wearer; and wherein the added microorganisms are added in such quantities and have such activity as to restrain the growth of undesirable species of microorganisms to such an extent as to prevent the generation of undesirable odors in the absorbent diaper.

8. The absorbent diaper according to claim 7, wherein the microorganisms exhibiting antagonistic properties are placed in the outer sheet of the absorbent article.

9. The absorbent diaper according to claim 7, wherein the microorganisms exhibiting antagonistic properties are placed in the absorbent structure of the absorbent article.

10. The absorbent diaper according to claim 7, wherein the microorganisms exhibiting antagonistic properties are placed in a loose insert product in the absorbent article.

11. The absorbent diaper according to claim 7, wherein the microorganisms exhibiting antagonistic properties are placed between two layers in the absorbent article.

12. In an absorbent diaper including added microorganisms, the improvement wherein the added microorganisms are selected from the group consisting of *Lactobacillus acidophilus, Lactobacillus curvatus, Lactobacillus plantarum,* and *Lactococcus lactis,* and exhibit, when the absorbent diaper is worn regularly by a wearer, antagonistic properties against undesirable strains of microorganisms selected from the group consisting of *Proteus mirabilis, Proteus vulgaris, Escherichia coli, Candida albicans,* and the genera Klebsiella, Enterococcus, Staphylococcus, Streptococcus and Pseudomonas, said strains of microorganisms being present or arising in the absorbent diaper or in the urogenital zone of the wearer of said absorbent diaper; and wherein the number of added microorganisms per absorbent diaper exceeds $10^6$ cfu so as to restrain the growth of undesirable species of microorganisms to such an extent as to prevent the generation of undesirable odors in the absorbent diaper.

* * * * *